(12) United States Patent
Blocher et al.

(10) Patent No.: US 10,390,820 B2
(45) Date of Patent: Aug. 27, 2019

(54) MEDICAL INSTRUMENT FOR MICROINVASIVE SURGICAL INTERVENTIONS

(75) Inventors: Martin Blocher, Tuttlingen (DE); Sebastian Wagner, Bretten (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 408 days.

(21) Appl. No.: 13/078,730

(22) Filed: Apr. 1, 2011

(65) Prior Publication Data

US 2011/0245812 A1 Oct. 6, 2011

(30) Foreign Application Priority Data

Apr. 1, 2010 (DE) .................. 10 2010 013 917

(51) Int. Cl.
*A61B 17/06* (2006.01)
*A61B 17/29* (2006.01)
*A61B 17/00* (2006.01)

(52) U.S. Cl.
CPC ........ *A61B 17/06109* (2013.01); *A61B 17/29* (2013.01); *A61B 2017/00738* (2013.01); *A61B 2017/00805* (2013.01); *A61B 2017/2901* (2013.01); *A61B 2017/2904* (2013.01)

(58) Field of Classification Search
CPC ....... A61B 19/22; A61B 1/313; A61B 1/3132; A61B 17/06109; A61B 17/29
USPC .............................................. 606/1; 600/130
See application file for complete search history.

(56) References Cited

U.S. PATENT DOCUMENTS

| 6,585,717 | B1 | 7/2003 | Wittenberger et al. |
| 6,595,984 | B1* | 7/2003 | DeGuillebon .................... 606/1 |
| 2004/0044350 | A1* | 3/2004 | Martin .................... A61B 50/30 606/139 |
| 2004/0215186 | A1* | 10/2004 | Cornelius .......... A61B 18/1492 606/41 |
| 2007/0156019 | A1* | 7/2007 | Larkin ................... B25J 19/025 600/104 |
| 2007/0197866 | A1* | 8/2007 | Park .............................. 600/114 |
| 2008/0172033 | A1* | 7/2008 | Keith et al. ................... 604/506 |

(Continued)

FOREIGN PATENT DOCUMENTS

DE 69725087 T2 6/2004
DE 202009007592 U1 8/2009
(Continued)

OTHER PUBLICATIONS

Definition of Base. Merriam-Webster Dictionary, retrieved on Apr. 28, 2016; Retrieved from the Internet: <http://www.merriam-webster.com/dictionary/base>.*

(Continued)

*Primary Examiner* — Gary Jackson
*Assistant Examiner* — Sebastian X Lukjan
(74) *Attorney, Agent, or Firm* — Whitmyer IP Group LLC

(57) ABSTRACT

A shaft for a medical instrument for a minimally invasive procedure includes a proximal end that is mechanically connectable or connected with an operational device and a distal end that is connectable or connected with a tool, whereby the shaft comprises a bent portion and whereby no plane exists from which the center points of all cross-sections of the shaft are at a lesser distance than one-third of a diameter of the shaft.

16 Claims, 3 Drawing Sheets

(56) References Cited

U.S. PATENT DOCUMENTS

| | | | |
|---|---|---|---|
| 2009/0054733 A1* | 2/2009 | Marescaux | A61B 17/29 600/141 |
| 2009/0082634 A1* | 3/2009 | Kathrani et al. | 600/207 |
| 2009/0105816 A1* | 4/2009 | Olsen | A61B 17/00234 623/2.37 |
| 2011/0092963 A1* | 4/2011 | Castro | A61B 17/3421 606/1 |

FOREIGN PATENT DOCUMENTS

| | | |
|---|---|---|
| EP | 2087834 A1 | 8/2009 |
| WO | 2005079702 A1 | 9/2005 |
| WO | 2006100658 A2 | 9/2006 |

OTHER PUBLICATIONS

European Search Report; Application No. EP 11 16 0058; dated Jul. 13, 2011; 5 pages.

\* cited by examiner

MEDICAL INSTRUMENT FOR MICROINVASIVE SURGICAL INTERVENTIONS

CROSS-REFERENCE TO RELATED APPLICATIONS

The present application claims priority of German patent application No. 10 2010 013 917.3 filed on Apr. 1, 2010, the content of which is incorporated herein by reference.

FIELD OF THE INVENTION

The present invention relates to a medical instrument for a minimally invasive procedure, in particular for a procedure by means of several instruments inserted through a single access opening, and to a shaft for such a medical instrument.

BACKGROUND OF THE INVENTION

Minimally invasive procedures, for example laparoscopic surgical interventions, were originally performed via several small openings. For example, an endoscope was inserted through a central access opening and medical instruments were inserted through one, two, or more lateral access openings. The arrangement of an endoscope centrally and of two instruments from the side is also occasionally referred to as triangulation. Increasingly, however, efforts are made to reduce the number of access openings. For example, in laparoscopic surgery only one central access opening is now used, through which an endoscope and as a rule several instruments are inserted simultaneously. For reasons of space, these instruments cannot be completely straight. With straight instruments whose middle portions are positioned in a small access opening, the comparatively voluminous operational devices at the proximal ends make it difficult or impossible to move the distal ends together. Therefore instruments with a curved shaft have been developed.

Curved shafts for surgical instruments are described in WO 2006/100658 A2, in EP 2 087 834 A1, and in DE 20 2009 007 592 U1.

Curved shafts can constitute a marked improvement over straight shafts, in particular in minimally invasive procedures with several instruments in a single access opening. There remains, however, a mutual obstruction among the instruments, in particular concerning the distal ends with the tools, the center portions of the shafts that are positioned in the access opening, and the proximal ends of the instruments with operational devices. Medical staff must constantly keep this potential or actual mutual obstruction in mind in operating the instruments. This means, for one thing, that part of the medical staff's attention is always directed at careful and anticipatory operation of the medical instruments and, for another thing, that certain movements of the medical instruments must be avoided because of space restrictions or cannot be performed. Neither situation is tolerable for medical staff who need to function with concentration, efficiency, and the avoidance of exhaustion.

SUMMARY OF THE INVENTION

An object of the present invention consists in providing an improved shaft, an improved medical instrument, and improved surgical instruments.

This object is achieved through the content of the independent claims.

Refinements are indicated in the dependent claims.

The present invention is based on the recognition that in many situations, mutual obstruction of several medical instruments is caused by their two-dimensional format. From the viewpoint of production, transport, and storage of medical instruments, it can be advantageous if their shafts are of two-dimensional form. It is also not obvious that two-dimensional configuration of the shafts of medical instruments increases their mutual obstruction or that three-dimensional configuration of the shafts of medical instruments reduces their mutual obstruction. However, a precise and impartial analysis of typical situations arising in practice with several medical instruments in an access opening and empirical investigations with three-dimensionally shaped shafts, surprisingly, resulted in reduced mutual obstruction even when the shafts had only relatively minor deviations from a purely two-dimensional format. Each type of deviation in format from a purely two-dimensional shape—whether in a distal portion of the shaft that is foreseen for positioning in the body, in a center portion that is foreseen for positioning in an access opening, or in a proximal portion foreseen for positioning outside the body being treated—has its specific advantages.

A shaft for a medical instrument for a minimally invasive procedure includes a proximal end that can be or is mechanically connected with an operational device and a distal end that can be or is connected with a tool, in such a way that no plane exists from which the center points of all cross-sections of the shaft are at a smaller distance than one-third of a diameter of the shaft.

The shaft is rigid, that is, not flexibly reshapable by the forces and moments that arise in the expected use. The shaft is in particular configured for an exploratory, surgical, therapeutic or other medical procedure through a single access opening.

The cross-sections are based on planes of intersection that are cut perpendicularly by the midline formed by the center points. The center point of a cross-section, independently of any hollow spaces in the shaft, is the geometric center point of the simply connected level surface bounded by the outer contour of the cross-section. In particular, all cross-sections of the shaft or at least their outer contours are equal or essentially equal. For example, all cross-sections are circular with the same radius.

In the case of a cross-section that varies along the shaft, the diameter existing in the particular cross-section is to be taken as the basis with respect to comparing the distance of the center point of the cross-section from a plane with the diameter of the shaft. In a non-circular cross-section, the diameter is taken to be the diameter of the smallest circle that completely surrounds the cross-section.

In the shaft described here, there exists in particular no plane from which the center points of all cross-sections of the shaft are at a lesser distance than a half-diameter of the shaft.

In some embodiments the center points of the cross-sections lie in one or more segments of the shaft, in particular also in curved segments of the shaft, in precisely a plane whereby at least one segment of the shaft exists in which the center points of the cross-sections are at a distance of at least one-third or at least one-half of the diameter of the shaft.

In particular on the basis of the following description of embodiments, it becomes clear that the aforementioned deviation of the shaft from the straight shape markedly reduces or even can avoid the mutual obstruction of the shafts of two medical instruments. Here the deviation of the shaft from the straight form is not necessarily large in many cases. Even a deviation of one-third, one-half, or an entire diameter of the shaft can have the positive effects described here.

Here the additional production expense incurred for three-dimensional format has proved in a few cases to be lower than previously assumed. Especially at lesser deviations from a straight configuration, the advantages of the straight format can still be largely retained with respect to transport and storage. In any case, slight disadvantages or a moderate additional cost are offset by marked advantages in handling. Mutual obstruction or discomfort or restricted mobility of the shafts of several medical instruments can arise more seldom or with less probability.

A shaft as described here can comprise a proximal portion, a center portion, and a distal portion, whereby the distal portion and the center portion lie in a plane from which the proximal portion deviates.

The proximal portion extends to the proximal end of the shaft and is foreseen for positioning outside a body to be treated with the expected application. The distal portion extends to the distal end of the shaft and is foreseen for positioning in the body to be treated with the expected application. The center portion lies between the proximal portion and the distal portion and in particular borders on both. The center portion is especially foreseen for positioning in the access opening or in the area of the access opening. The distal portion and the center portion lie in particular in precisely a plane that is unequivocally defined by the center points of all cross-sections in the distal portion and in the center portion.

A deviation of the shaft from the straight format in the proximal portion makes possible, for example, a crossing of two shafts in the proximal portion without requiring a lateral displacement of the proximal ends of the shafts or of operational devices positioned on them. If both shafts deviate in the proximal portion from the straight format, a deviation in each case by just a half-diameter can be sufficient.

A shaft as described here can comprise a proximal portion, a center portion, and a distal portion so that the distal portion and the proximal portion lie in a plane from which the center portion deviates.

As mentioned, in the foreseen application the center portion of the shaft is positioned in a narrow access opening (for example, a trocar or a trocar sleeve) together with one or more other shafts of an endoscope and/or of other medical instruments. If two shafts in this center portion have a straight format, they can be contiguous with one another either in linear shape or at several locations set apart from one another. In a relative movement of both shafts, this can increase the friction resistance or lead to a discontinuous change of relative rotation points and lever arms. Either of these is undesired, as a rule, because they restrict the sensitivity and precision with which the shafts can be moved in relation to one another.

If the shape of one or both shafts deviates from a plane in the center portion, the shafts as a rule can be contiguous with one another only at one site. Tipping or sliding of both shafts with respect to one another, in this case, has a minimal friction and has as a consequence no displacement or in any case a continuous displacement of a relative axis of rotation and accordingly no modification or in any case a continuous modification of the lengths of the lever arms. A deviation of the shaft from the straight shape can thus increase sensitivity and precision in handling and in the activities performed by means of the shaft.

A shaft as described here can comprise a proximal area, a center area, and a distal area, whereby the center area and the proximal area lie in a plane from which the distal area deviates.

A deviation of the shaft from the straight format in the distal portion can simplify a crossing of the shafts of two medical instruments in the distal portion. As soon as each of the two shafts deviates by a half-diameter from the straight format, a crossing of the two shafts can become possible without a lateral displacement of its distal ends or of tools at their distal ends. The advantages are therefore similar to the aforementioned advantages of a deviation of the shaft from the straight format in the proximal area.

The advantages of the deviation of the shaft from the straight shape in the distal portion can, however, be still more important because fewer alternatives exist. In the proximal area, that is, in the foreseen application outside the body to be treated, the shafts of medical instruments can be shaped in such a way that a crossing can be avoided in most cases. Crossing in the distal area, however, can be avoided in many cases only at great expense, for example by exchanging both medical instruments. However, exchanging two medical instruments during a procedure costs time, interrupts the operational sequence, demands rethinking by the medical staff, and increases the risk of injury for the patient. These disadvantages can be reduced or avoided by a deviation of the shaft from the straight format in the distal portion.

In a shaft as described here, at least one portion can be of helical configuration.

A helix is a spatial curve with constant curvature on a sheath surface of a cylinder. A segment of the shaft is helically configured when the center points of all cross-sections of the shaft lie on a helix. The helically configured segment of the shaft can be the proximal, the center, or the distal portion in the sense of the description above. In addition, the entire shaft or nearly the entire shaft can be of helical configuration. However, in all the embodiments described here, it can be advantageous in view of production if short portions (with a length, for example, of a few millimeters or few centimeters) are straight at the ends of the shaft.

A helical configuration of the shaft or of a portion of the shaft makes possible, depending on the radius and the pitch of the helix, on the one hand a positioning of the distal ends of several shafts and of tools connected thereto, similarly as in classical triangulation, in which the tools of several medical instruments extend laterally into the field of vision of a central endoscope. At the same time two shafts that are helically configured in the center portion with equal winding direction are contiguous with one another only at one point in the access opening in almost all relative positions. A relative displacement or tipping of two or more spiral-shaped shafts in the access opening is therefore possible with minimal friction and without spasmodic change of effective lever lengths.

As a rule, it is advantageous to use several shafts with helically configured portions with equal winding direction, equal or similar radii, and equal or similar pitches. Especially positive experience occurs with shafts that form essentially a half-rotation over nearly their entire length, so that the ratio between the radius and the pitch lies between 1:10 and 1:20.

In a shaft as described here, in a connected portion that includes at least half of the length of the shaft, the derivative of the normed tangential vector of the midline of the shaft along the midline can continuously or discontinuously rotate in one direction or, in straight segments, can be equal to zero.

As previously mentioned, the midline of the shaft is the quantity of the center points of all cross-sections. An example of a shape of the shaft in which the normed tangential vector rotates continuously in one direction is the aforementioned helical shape. Deviating from a helical shape, the derivative of the normed tangential vector along the midline can change spasmodically or continuously both with respect to its amount and with respect to its direction. For example, a series of several portions that each is curved within a plane can under some circumstances entail a lower production cost than a helical structure or another structure in which the normed tangential vector rotates continuously.

In a shaft as described here, the proximal end and the distal end can be aligned parallel to one another or can form an angle of at most 10 degrees.

The direction of an end of a shaft is the direction of the tangential vector of the midline at the end. Parallel or even coaxial alignment of both ends of a shaft encourage particularly intuitive operation by medical staff. Even at the helical configuration of a portion of the shaft as described above, transition areas can be connected on the helical portion so that both ends of the shaft can be aligned parallel or even coaxially, even when the helical portion includes no full rotation.

A shaft as described here can include a first portion in which the shaft runs parallel to a first plane, and a second portion in which the shaft runs parallel to a second plane, whereby the first plane and the second plane are not parallel to one another.

In particular, the shaft is curved both in the first portion and in the second portion. In mathematical terms, the vector product of the tangential vector and of the derivative of the tangential vector has a first direction in the first portion and a second direction in the second portion, said second direction differing from the first direction. A curvature within a plane can in many cases be realized with minor production costs, so that a series of portions within which the shaft runs in each case parallel to a plane can be produced at reasonable cost.

The first plane and the second plane in particular form an angle of at least 10 degrees.

The angle between two planes is the angle between their surface normals. Greater angles of at least 20 degrees or at least 30 degrees or at least 60 degrees can be advantageous.

A medical instrument includes a shaft as described here and at least either an operational device that is connectable or connected with the proximal end of the shaft, or a tool that is connectable or connected with the distal end of the shaft.

A surgical utensil includes two medical instruments as described here, whereby, in the shafts of both medical instruments in portions corresponding to one another in terms of the distances from the distal ends of the shafts, the derivatives of the normed tangential vectors of the midlines of the shafts rotate continuously or discontinuously in the same direction along the midline.

The same-direction rotation of the derivative of the normed tangential vectors reduces the mutual obstruction of two shafts.

In a surgical utensil as described here, the shafts of both medical instruments, in portions corresponding to one another in terms of the distances from the distal ends of the shafts, are of helical configuration and have the same rotation direction.

BRIEF DESCRIPTION OF THE DRAWINGS

Hereinafter, embodiments are explained in greater detail with reference to the appended drawings, which are as follows.

DETAILED DESCRIPTION OF THE INVENTION

Figure 1:
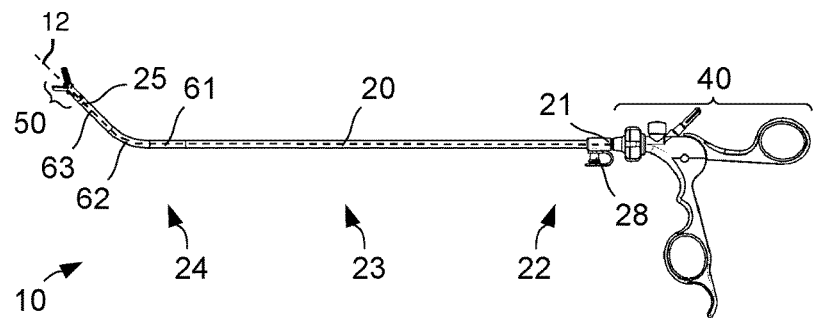
FIG. 1 shows a schematic depiction of a medical instrument.

FIGS. 1 through 12 show schematic depictions of four different medical instruments. Each three successive drawings show schematic axonometric depictions of a medical instrument from three different perspectives or directions. The planes of projection of the three figures referring in each case to the same medical instrument, FIG. 1 through 3 or 4 through 6 or 7 through 9 or 10 through 12, are perpendicular to each other. The planes of projection of FIGS. 2, 5, 8, and 11 correspond to one another. The planes of projection of FIGS. 3, 6, 9, and 12 correspond to one another.

Each of the medical instruments 10 illustrated in FIG. 1 through 3 or 4 through 6 or 7 through 9 or 10 through 12 includes a shaft 20 with a proximal end 21 and a distal end 25 and with an essentially constant circular cross-section between the proximal end 21 and the distal end 25. On the proximal end 21 the shaft 20 in each case can comprise a flushing connection 28. The shaft 20 includes a longitudinal axis 12 extending between the proximal end 21 and the distal end 25. At least a portion of the shaft 20 is curved along the longitudinal axis 12.

An operational device 40 is connected with the proximal end 21, and a tool 50 is connected with the distal end 25 of the shaft 20. Both the operational device 40 and the tool 50 can be connected permanently or not detachably without disruption with the shaft 20. Both the operational device 40 and the tool 50 can alternatively be connected detachably without disruption with the shaft 20, for example by bayonet and/or catch-lock connections.

In the illustrated medical instruments, a plug-in connection is provided between the proximal end 21 of the shaft 20 and the operational device 40, along with rotatability of the shaft in the operational device 40, so that a detachable catch-lock connection holds the shaft 20 on the operational device 40. The operational devices 40 of all illustrated medical instruments 10 have mutually corresponding characteristics, which are described in greater detail hereinafter.

In part, distinctions are made hereinafter between a proximal portion 22, a center portion 23, and a distal portion 24 of the shaft 20. The proximal portion 22 extends as far as or essentially as far as the proximal end 21 of the shaft 20. The distal portion 24 extends as far as or essentially as far as the distal end 25. The center portion 23 extends essentially between the proximal portion 22 and the distal portion 24. In the expected application of the medical instruments 10, the proximal portion 22 of the shaft 20 is intended to be positioned outside a body that is to be treated; the distal portion 24 is intended to be positioned in a natural or artificial cavity in the body to be treated; the center portion 23 is intended to be positioned in an access opening, for example in a trocar or trocar sleeve.

Figure 2:
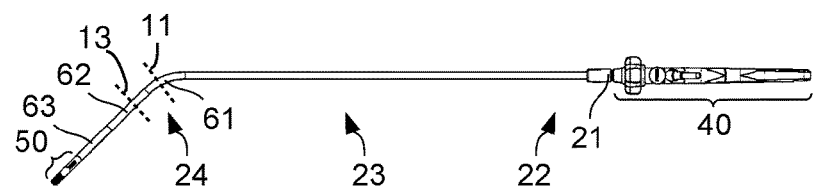
FIG. 2 shows another schematic depiction of the medical instrument from FIG. 1.
Figure 3:
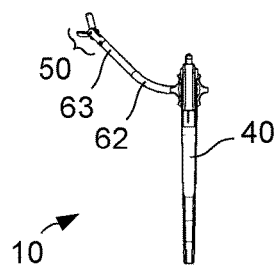
FIG. 3 shows another schematic depiction of the medical instrument from FIGS. 1 and 2.

FIGS. 1 through 3 show schematic axonometric depictions of a medical instrument 10 whose shaft 20 is straight in the proximal portion 22 and in the center portion 23. Two curved segments 61, 62 and an additional, short straight segment 63 are connected distally to the straight portion. Inside the first curved segment 61 and inside the second curved segment 62, the shaft has an essentially straight shape. Inside the first curved segment 61, the center points of all cross-sections 11 lie in a single, first plane (i.e., in FIG. 2, the plane of the page); inside the second curved segment 62, the center points of all cross-sections 13 of the shaft 20 lie in a single, second plane (i.e., in FIG. 1, the plane of the page). Both the first plane and the second plane are unequivocally defined on the basis of the curvature of the first curved segment 61 and of the second curved segment 62. On the basis of the straight form of the shaft 20 proximally from the first curved segment 61 and distally from the second curved segment 62, the center points of all cross-sections 11 of the first curved segment 61 and proximally from the same lie in the first plane and the center points of all cross-sections 13 of the shaft 20 lie in the second curved segment 62 and distally from the same in the second plane.

The first plane and the second plane are not parallel to one another. In FIG. 1 it can be recognized that the first plane is perpendicular to the plane of projection of FIG. 1, so that the first curved segment 61 appears straight in FIG. 1. It can be recognized in FIG. 2 that the second plane is perpendicular to the plane of projection of FIG. 2, so that the second curved segment 62 appears straight in FIG. 2.

It can be recognized in comparing FIGS. 1 through 3 that no plane exists in which the center points of all cross-sections of the shaft 20 are found. Instead, the distal portion 24 of the shaft 20 has a suggestion of a screw-like shape. The derivative of the normed tangential vector of the midline of the shaft 20 made up of the center points of all cross-sections lies in the first curved segment 61 in the plane of projection of FIG. 2 and is perpendicular to the plane of projection of FIG. 2 at the proximal end of the second curved segment 62. The derivative of the tangential vector of the midline rotates suddenly by 90 degrees in clockwise direction at the transition between the first curved segment 61 and the second curved segment 62.

The shape of the shaft 20 of the medical instrument 10 in FIGS. 1 through 3 makes possible a collision-free or unhindered crossing of the distal portion 25 of the shaft 20 with the distal portion of a shaft of an additional medical instrument, in particular when the shaft of the second medical instrument is straight or at least is of screw-like or approximately screw-like configuration in the distal portion with the same rotation direction. It can be particularly advantageous to make simultaneous use of two of the same medical instruments 10 that both correspond to the foregoing depictions in FIGS. 1 through 3.

Figure 6:
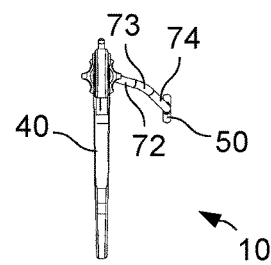
FIG. 6 shows another schematic depiction of the medical instrument from FIGS. 4 and 5.
Figure 4:
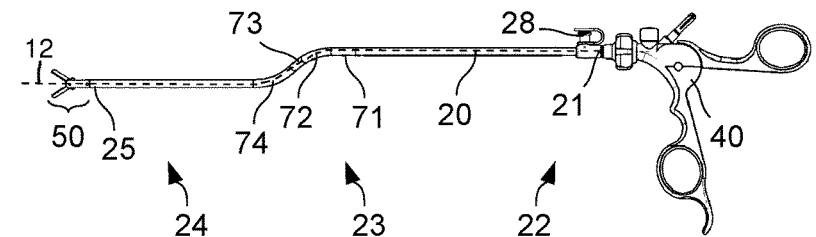
FIG. 4 shows a schematic depiction of an additional medical instrument.
Figure 5:
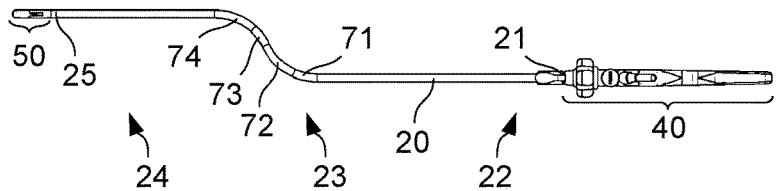
FIG. 5 shows another schematic depiction of the medical instrument from FIG. 4.

FIGS. 4 through 6 show schematic axonometric depictions of an additional medical instrument 10, which resembles in some characteristics the medical instrument presented above with reference to FIGS. 1 through 3. Contrary to the medical instrument presented above and in FIGS. 1 through 3, the shaft 20 of the medical instrument 10 shown in FIGS. 4 through 6 is straight in the proximal portion 22 and in the distal portion 24 and is curved in the center portion 23.

In the center portion 23 the shaft 20 comprises four curved segments 71, 72, 73, 74, within which the center points of all cross-sections of the shaft 20 are each found in a plane. A first plane, in which the center points of all cross-sections of the shaft 20 lie inside the first curved segment 71 and proximally from the same, is perpendicular to the plane of projection of FIG. 4. Therefore the first curved segment 71 in FIG. 4 appears straight. It can be recognized in FIG. 6 that a second plane, in which the center points of all cross-sections of the shaft 20 lie in the second curved segment 72, and a fourth plane, in which the center points of all cross-sections of the shaft 20 lie in the fourth curved segment 74, are each perpendicular to the plane of projection of FIG. 6. Therefore both the second curved segment 72 and the fourth curved segment 74 appear straight in FIG. 6.

Upon close observation of FIGS. 4 through 6 it can be recognized that the shaft 20 has an approximately right-rotating screw-like shape or a helical shape in the center portion 23. The derivative of the normed tangential vector of the midline of the shaft 20 made up of the center points of all cross-sections rotates discontinuously along this midline in counterclockwise direction. At the transitions between the curved segments 71, 72, 73, 74, the direction of the derivative of the normed tangential vector rotates spasmodically at angles between 20 and 120 degrees to the right or in clockwise direction.

The shape of the shaft 20 of the medical instrument 10 presented with reference to FIGS. 4 through 6 facilitates a low-friction and unimpeded relative movement of the shaft 20 of the illustrated medical instrument 10 and of the shaft or shafts of one or more additional medical instruments that are positioned together in a close access opening. This is true in particular when the shaft or shafts of the one or more medical instruments are straight or similarly curved in the center portion like the shaft 20 of the medical instrument presented with reference to FIGS. 4 through 6. In particular, a screw-shaped or helical or approximately screw-shaped or helical configuration with the same rotation direction of all shafts in the center portion can be advantageous. In most or even in most of the relative arrangements of several shafts, this shape makes possible a mutual touching in only one point each or at only one location each. In comparison with a possible mutual touching of two shafts in at least two points at a distance from one another, this results on the one hand in markedly reduced friction. An additional advantage can consist in the fact that, as long as a mutual touching of two shafts occurs in only one point, a sudden displacement of a momentary axis of a relative rotation of two shafts and a sudden change in the lengths of lever arms is not possible.

Figure 7:
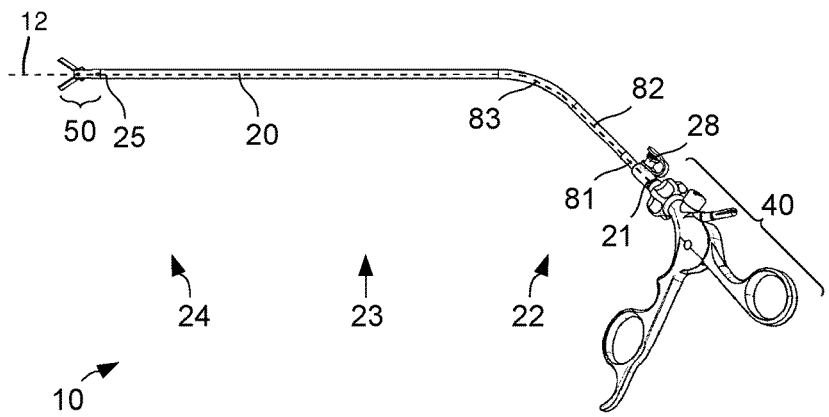
FIG. 7 shows a schematic depiction of another medical instrument.
Figure 8:
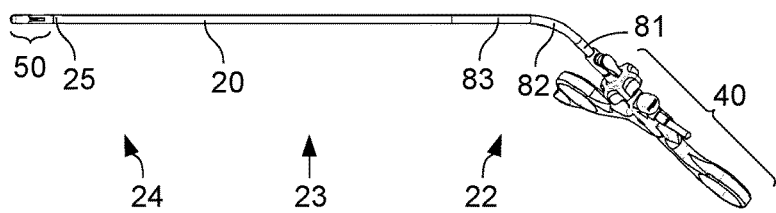
FIG. 8 shows another schematic depiction of the medical instrument from FIG. 7.
Figure 9:
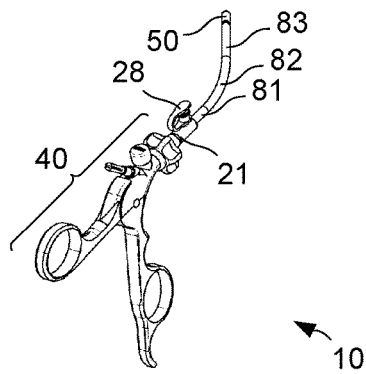
FIG. 9 shows another schematic depiction of the medical instrument from FIGS. 7 and 8.

FIGS. 7 through 9 show schematic axonometric depictions of a medical instrument 10 that resembles in a few characteristics the medical instrument presented above with reference to FIG. 1 through 3 or 4 through 6. Unlike in the medical instrument presented above with reference to FIGS. 1 through 3 and 4 through 6, the shaft 20 of the medical instrument 10 shown in FIGS. 7 through 9 is curved in the proximal portion 22 and in the center portion 23 and straight in the distal portion 24.

In the proximal portion 22 the shaft 20 comprises a short straight segment 81, a first curved segment 82, and a second curved segment 83. In the first curved segment 82 and in the proximally adjoining short straight segment 81 of the shaft 20, the center points of all cross-sections of the shaft 20 lie in a single, first plane. In the second curved segment 83 and distally from the same, the center points of all cross-sections of the shaft 20 lie in a second plane. In comparing FIGS. 7 and 8 it is recognizable that the first plane is perpendicular to the plane of projection of FIG. 7. Therefore the first curved segment 82 appears straight in FIG. 7. It is further recognizable that the second plane is perpendicular to the plane of projection of FIG. 8. Therefore the second curved segment 83 appears straight in FIG. 8.

In comparing FIGS. 7 through 9 it can be recognized that the shaft 20 of the medical instrument 10 shown in FIGS. 7 through 9 has approximately the shape of a left-threaded screw or helix. The derivative of the normed tangential vector of the midline of the shaft 20 made up of the center points of all cross-sections rotates spasmodically by approximately 90 degrees in counterclockwise direction at the transition between the first curved segment 82 and the second curved segment 83.

The shape of the shaft 20 of the medical instrument 10 presented with reference to FIGS. 7 through 9 can make possible an especially low-obstruction or obstruction-free relative movement of the shafts of several medical instruments that are used simultaneously in an access opening. This is true in particular when the medical instrument 10 presented with reference to FIGS. 7 through 9 is used together with one or more additional medical instruments whose shafts are configured corresponding to or similar to the shaft 20 of the medical instrument 10 presented with reference to FIG. 7 through 9 or straight. In particular, the illustrated shape of the shaft 20 can make possible or facilitate crossing of the proximal portions of two shafts without lateral displacement.

Figure 10:
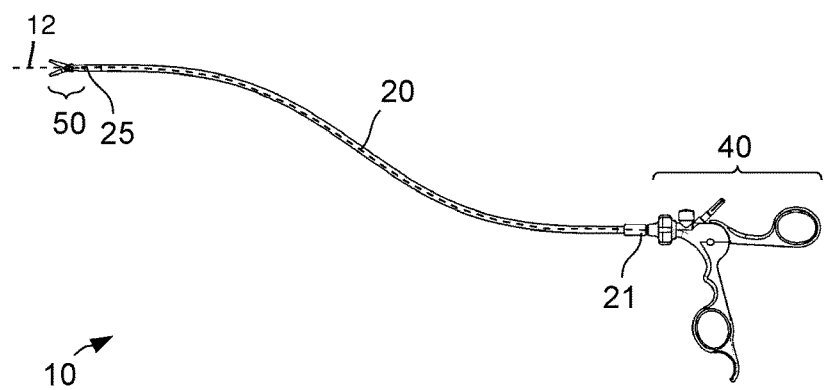
FIG. 10 shows a schematic depiction of another medical instrument.
Figure 11:
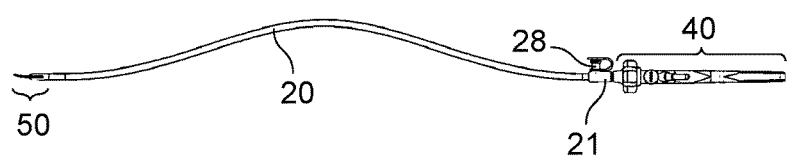
FIG. 11 shows another schematic depiction of the medical instrument from FIG. 10.
Figure 12:
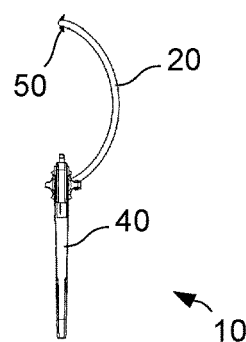
FIG. 12 shows another schematic depiction of the medical instrument from FIGS. 10 and 11.

FIGS. 10 through 12 show schematic axonometric depictions of an additional medical instrument 10, which is similar in a few characteristics to the medical instruments presented above with reference to FIG. 1 through 3 or 4 through 6 or 7 through 9. Contrary to the medical instruments presented above with reference to FIGS. 1 through 9, the shaft 20 of the medical instrument shown in FIGS. 10 through 12 has an essentially helical shape in a large, center portion of its length. As a result of transitional arcs and straight portions at the proximal end 21 and at the distal end 25, which are scarcely recognizable in the drawings, the proximal end 21 and the distal end 25 of the shaft 20 have the same orientation or are parallel to one another.

Advantages of the medical instrument 10 shown in FIG. 10 through 12 resemble or correspond largely to the advantages of the medical instruments presented above with reference to FIGS. 1 through 9 or combinations thereof. In particular, the shafts of two or three medical instruments as presented with reference to FIGS. 10 through 12 or to FIGS. 4 through 6 can be positioned in an access opening in such a way that they touch one another only at one point or in one location. This is the case, for example, when two shafts are positioned rotated with respect to one another by 180 degrees or three shafts are positioned rotated with respect to one another by approximately 120 degrees each. On the basis of the illustrated shape of the shafts, the latter cross one another in the access opening at wide angles, so that even with fairly large relative rotations or sliding, a mutual touching of two shafts always occurs only at one point or in one location.

Simultaneously the illustrated non-straight shape of the shaft of at least one of the simultaneously used medical instruments can make possible a crossing of the distal portions 24 and/or of the proximal portions 22 of the shafts 20 without a relative lateral displacement.

Figure 13:
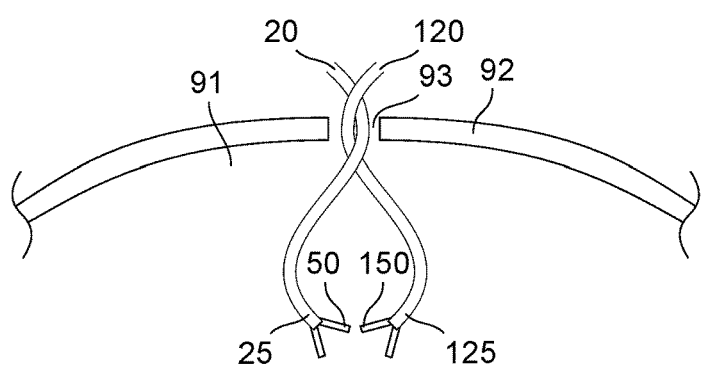
FIG. 13 shows a schematic depiction of two medical instruments in the foreseen application.

FIG. 13 shows a schematic depiction of an example of a simultaneous use of two medical instruments as presented for example above with reference to FIGS. 4 through 6 or 10 through 12. The medical instruments are used, for example, for an exploratory or surgical minimally invasive procedure in an artificial or natural cavity 91 in the body of a patient. The cavity 91 is bounded by a wall 92 in which there is a natural or artificial access opening 93. The wall is, for example, the abdominal wall of the patient.

Shafts 20, 120 of two medical instruments are introduced through the access opening 93 into the cavity 91. In the center portion or in the portion of the access opening 93, the two shafts 20, 120 are positioned wound around one another in the manner of a double helix. With sufficient curvature radii of the shafts 20, 120, the shafts 20, 120 touch one another at most at one point.

If both shafts 20, 120 have a flat shape, that is, if the center points of all cross-sections of the shaft 20 lie in a first plane and the center points of all cross-sections of the shaft 120 lie in a second plane, these two planes intersect in the portion of the access opening 93, but could be non-parallel to one another. The distal ends 25, 125 of the shafts 20, 120 and the tools 50, 150 positioned on them could therefore not be moved together. In most minimally invasive procedures, however, it is required that the tools 50, 150 at the distal ends 25, 125 of the shafts 20, 120 of two or more medical instruments can be approached to one another up to a very small mutual distance.

In the case of straight shafts 20, 120, contrary to the depiction in FIG. 13 a parallel positioning of the planes of the shafts 20, 120 is conceivable. Then the shafts 20, 120 could, however, touch at two points, with the aforementioned disadvantages.

Only the deviation of at least one of the shafts 20, 120 from a straight shape makes possible simultaneously the illustrated arrangement of the two shafts 20, 120 at least partly surrounding one another in the access opening and a freedom to approach the distal ends 25, 125 of the shafts 20, 120 and the tools positioned thereon.

What is claimed is:

1. A system for a minimally invasive medical procedure in a body cavity bounded by a body cavity wall with an access opening, the system comprising:
   two medical instruments, each including a rigid shaft having:
      a proximal end that is mechanically connectable or connected with an operational device of the respective medical instrument;
      a distal end that is connectable or connected with a tool of the respective medical instrument; and
      a longitudinal axis extending between the proximal end and the distal end, at least a portion of the rigid shaft being curved along the longitudinal axis;
      wherein no plane exists from which respective center points of all cross-sections of the rigid shaft defined in respective planes perpendicular to the longitudinal axis are at a respective distance less than one-third of a diameter of the rigid shaft;

wherein no plane exists in which all respective center points of all cross-sections of the rigid shaft defined in respective planes perpendicular to the longitudinal axis are located;

wherein the proximal end and the distal end are oriented parallel to one another or form an angle of at most 20 degrees to one another; and wherein the rigid shaft comprises a proximal portion, a center portion, and a distal portion and wherein the distal portion and the proximal portion lie in a plane from which the center portion deviates;

wherein respective helical portions of the rigid shafts are configured to be wound around one another in a double helix manner to permit simultaneous use of the rigid shafts through the access opening of the body cavity wall.

2. The rigid shaft of claim 1, wherein each rigid shaft has a midline that is the quantity of center points of all cross-sections of the rigid shaft defined in respective planes perpendicular to the longitudinal axis, and wherein in a contiguous area that includes at least half of the length of the rigid shaft, the rigid shaft rotates continuously or discontinuously along the midline in one direction.

3. The rigid shaft of claim 1, wherein each rigid shaft is configured such that the proximal end is detachably connected via a catch-lock connection to the operational device.

4. The rigid shaft of claim 3, wherein the catch-lock connection is a plug-in connection of the respective medical instrument.

5. The rigid shaft of claim 1, wherein each rigid shaft is configured such that the distal end is detachably connected via a catch-lock connection to the tool of the respective medical instrument.

6. The rigid shaft of claim 5, wherein the catch-lock connection is a plug-in connection.

7. The rigid shaft of claim 1, wherein each rigid shaft is configured such that the distal end of the rigid shaft is made of at least two segments.

8. A system for a minimally invasive medical procedure in a body cavity bounded by a body cavity wall with an access opening, the system comprising:

two medical instruments, each including a rigid shaft having:
  a proximal end that is mechanically connectable or connected with an operational device of the respective medical instrument; and
  a distal end that is connectable or connected with a tool of the respective medical instrument;
  a longitudinal axis extending between the proximal end and the distal end, at least a portion of the rigid shaft being curved along the longitudinal axis;
  wherein the rigid shaft comprises a proximal portion having proximal cross-sections defined in respective planes perpendicular to the longitudinal axis, a central portion having central cross-sections defined in respective planes perpendicular to the longitudinal axis, and a distal portion having distal cross-sections defined in respective planes perpendicular to the longitudinal axis;
  wherein no plane exists in which respective center points of all proximal, central, and distal cross-sections defined in respective planes perpendicular to the longitudinal axis are located;
  wherein the respective center points of all distal cross-sections defined in respective planes perpendicular to the longitudinal axis and the respective center points of all proximal cross-sections defined in respective planes perpendicular to the longitudinal axis lie in a first plane from which at least a portion of the respective center points of the central cross-sections defined in respective planes perpendicular to the longitudinal axis deviate;
  wherein at least one of the respective center points of the central cross-sections is a respective distance of at least one-third of a diameter of the rigid shaft away from the first plane; and
  wherein the proximal end and the distal end are oriented parallel to one another or form an angle of at most 20 degrees to one another;
  wherein respective helical portions of the rigid shafts are configured to be wound around one another in a double helix manner to permit simultaneous use of the rigid shafts through the access opening of the body cavity wall.

9. The rigid shaft of claim 8, wherein each rigid shaft is configured such that the deviation of the distal portion and the proximal portion from the central portion reduces mutual obstruction of the rigid shaft with a second shaft of a second medical instrument when the rigid shaft and the second shaft of the second medical instrument are crossed.

10. The rigid shaft of claim 8, wherein each rigid shaft is configured such that the deviation of the distal portion of the rigid shaft has minimal friction with a distal portion of a second medical instrument when the rigid shaft and the second medical instrument are crossed.

11. The rigid shaft of claim 8, wherein each rigid shaft is configured such that the proximal portion is configured to be positioned outside a body that is to be treated, wherein the distal portion is configured to be positioned in a cavity inside the body that is to be treated, and wherein the central portion is configured to be positioned in an access opening.

12. A system for a minimally invasive medical procedure in a body cavity bounded by a body cavity wall with an access opening, the system comprising:

two medical instruments, each including a rigid shaft having:
  a proximal end of said rigid shaft mechanically connectable or connected with an operational device of the respective medical instrument;
  a distal end of said rigid shaft mechanically connectable or connected with a tool of the respective medical instrument;
  a longitudinal axis extending between the proximal end and the distal end, at least a portion of the rigid shaft being curved along the longitudinal axis;
  wherein the rigid shaft comprises a proximal portion having proximal cross-sections defined in respective planes perpendicular to the longitudinal axis, a central portion having central cross-sections defined in respective planes perpendicular to the longitudinal axis, and a distal portion having distal cross-sections defined in respective planes perpendicular to the longitudinal axis;
  wherein no plane exists in which respective center points of all proximal, central, and distal cross-sections defined in respective planes perpendicular to the longitudinal axis are located;
  at least one respective center point selected from one of the groups of:
    distal cross-sections defined in respective planes perpendicular to the longitudinal axis, proximal cross-sections defined in respective planes perpendicular to the longitudinal axis, or central cross-sections defined in respective planes perpendicular to the longitudinal axis;

the at least one respective center point lies at a position at least one-third of a diameter of the rigid shaft away from a first plane in which the respective center points of the other two non-selected groups lie; and wherein the proximal end and the distal end are oriented parallel to one another or form an angle of at most 20 degrees to one another;

wherein respective helical portions of the rigid shafts are configured to be wound around one another in a double helix manner to permit simultaneous use of the rigid shafts through the access opening of the body cavity wall.

13. The medical instrument of claim 12, wherein each rigid shaft is configured such that the at least one respective center point lies at a position at least one-half of the diameter of the rigid shaft away from the first plane.

14. The medical instrument of claim 12, wherein each rigid shaft is configured such that respective center points of all distal cross-sections defined in respective planes perpendicular to the longitudinal axis and respective center points of all central cross-sections defined in respective planes perpendicular to the longitudinal axis lie in the first plane.

15. The medical instrument of claim 12, wherein each rigid shaft is configured such that respective center points of all distal cross-sections defined in respective planes perpendicular to the longitudinal axis and respective center points of all proximal cross-sections defined in respective planes perpendicular to the longitudinal axis lie in the first plane.

16. The medical instrument of claim 12, wherein each rigid shaft is configured such that respective center points of all central cross-sections defined in respective planes perpendicular to the longitudinal axis and respective center points of all proximal cross-sections defined in respective planes perpendicular to the longitudinal axis lie in the first plane.

* * * * *